United States Patent [19]

Rechner et al.

[11] Patent Number: 5,274,163
[45] Date of Patent: Dec. 28, 1993

[54] PROCESS FOR THE PREPARATION OF DIALKYL CARBONATES

[75] Inventors: Johann Rechner; Alexander Klausener; Hans-Josef Buysch, all of Krefeld; Paul Wagner, Duesseldorf, all of Fed. Rep. of Germany

[73] Assignee: Bayer Aktiengesellschaft, Leverkusen, Fed. Rep. of Germany

[21] Appl. No.: 12,102

[22] Filed: Feb. 1, 1993

[30] Foreign Application Priority Data

Feb. 10, 1992 [DE] Fed. Rep. of Germany ....... 4203796

[51] Int. Cl.$^5$ .............................................. C07C 69/96
[52] U.S. Cl. .................................................... 558/277
[58] Field of Search ......................................... 558/277

[56] References Cited

U.S. PATENT DOCUMENTS

| | | | |
|---|---|---|---|
| 3,846,468 | 11/1974 | Perrotti et al. | 558/275 |
| 4,218,391 | 8/1980 | Romano et al. | 558/277 |
| 4,318,862 | 3/1982 | Romano et al. | 558/277 |
| 4,370,275 | 1/1983 | Stammann et al. | 558/277 |
| 5,142,087 | 8/1992 | Joerg et al. | 558/277 |

FOREIGN PATENT DOCUMENTS

| | | |
|---|---|---|
| 1206974 | 2/1986 | Canada . |
| 0090977 | 10/1983 | European Pat. Off. . |
| 02176541 | 4/1987 | European Pat. Off. . |
| 0460732 | 12/1991 | European Pat. Off. . |
| 0460735 | 12/1991 | European Pat. Off. . |
| 2110194 | 11/1971 | Fed. Rep. of Germany . |
| 2450856 | 4/1975 | Fed. Rep. of Germany . |
| 2743690 | 4/1978 | Fed. Rep. of Germany . |
| 3045767 | 6/1981 | Fed. Rep. of Germany . |
| 3926709 | 2/1991 | Fed. Rep. of Germany . |
| 1441356 | 6/1976 | United Kingdom . |

OTHER PUBLICATIONS

Ind. Eng. Chem. Prod. Res. Dev., 1980, 19, pp. 396–403.

*Primary Examiner*—Mary C. Lee
*Assistant Examiner*—Michael G. Ambrose
*Attorney, Agent, or Firm*—Sprung Horn Kramer & Woods

[57] ABSTRACT

A process is described for the preparation of dialkyl carbonates by oxidative carbonylation of the corresponding alcohol in the presence of a copper-containing catalyst at elevated temperature and elevated pressure, which process permits simple separation of the copper-containing catalyst by sedimentation, and of the reaction water in the case of methanol by simple distillation from the reaction solution.

20 Claims, 2 Drawing Sheets

PROCESS FOR THE PREPARATION OF DIALKYL CARBONATES

BACKGROUND OF THE INVENTION

1. Field of the Invention

The present invention relates to a process for the continuous preparation of dialkyl carbonates by reaction of the corresponding alkanol with oxygen and carbon monoxide in the presence of a copper-containing catalyst suspended or dissolved in the reaction medium, at elevated pressure and elevated temperature, in which the catalyst can be eliminated from the reaction medium by sedimentation and the reaction water in the particularly important case of methanol can be eliminated from the reaction medium by simple distillation.

2. Description of the Related Art

In the past years a series of processes have been developed for the preparation of dialkyl carbonates by the catalytic reaction of the starting materials alkanol, carbon monoxide and oxygen.

In DE-A 2 110 194, suitable catalysts mentioned are metal complexes selected from groups IB, IIB and VIIIB of the Periodic Table of the Elements, in particular those of the metals Cu, Ag, Au, Zn, Cd, Hg, Fe, Co and Ni, which can exist in two different oxidation states in redox reactions.

This process gives good yields with $Cu_2Cl_2$, but has the disadvantage that the separation of the highly expensive complex ligands and of the dissolved complexed catalyst from the reaction solution is laborious.

In DE-C 2 743 690, instead of the copper complex compounds, simple monovalent salts of copper are used as catalysts. Although this process variant gives good yields of dialkyl carbonates, the work-up of the reaction solution also poses great problems here, since the partially dissolved catalyst must be separated from the reaction solution. According to the teaching of the patent, this is carried out by filtering off the suspended fraction and rectifying or crystallising the dissolved catalyst. Since the catalyst-containing reaction solutions carry the catalyst into further parts of the plant, a high expenditure in terms of apparatus is required for the work-up of the reaction solution and of the catalyst. Because of the corrosive properties, all apparatuses (tanks, piping, distillation, crystallisation and filtration apparatuses) which come into contact with the catalyst must be composed of corrosion-resistant material. As a result, the process loses its attraction.

The same work-up problems also cause the use of synthesis gas instead of CO, as described in DE-C 3 045 767, to remain economically unattractive. The corrosion problems caused by the copper-containing catalyst during the workup of the reaction solution cause processes which include further additions to the catalyst (for example EP-A 217 651, EP-B 90 977, US-A 4 370 275) to be uneconomic.

DE-A 3 926 709 teaches a processing alternative to separating off the catalyst; in this case the copper-containing catalyst remains in the reactor. The dialkyl carbonate formed during the reaction, together with the reaction water and alkanol, is stripped from the reaction mixture by the reaction gas. This effect is generally achieved in that a gas stream of 20 to 30 l(S.T.P.)$CO/O_2$ of gas mixture per g of copper present in the reactor as copper catalyst is passed through the reaction mixture. Disadvantages of this process are the very high gas quantities which must be maintained in the circulation and the high energy costs caused as a result, and the problems of gas dispersion caused by the high gas quantities. In this procedure, the temperature and pressure of the reactor must additionally be controlled very exactly in order to be able to maintain the liquid level in the reactor, since even small variations in reactor temperature or in pressure lead to markedly changed output rates. Moreover, in this case, a relatively large quantity of water accumulates in the reactor, which decreases the selectivity of the reaction.

The reaction is carried out in the described processes in autoclaves as pressure vessel. These expensive reactors have the disadvantage that the mixing of the reaction medium is carried out with the aid of stirrers and internals which are subjected to high wear. In addition, the stirrer unit especially represents a potential source of leakage.

EP 460 732 A1 and EP 460 735 A2 describe a process in which, analogously to DE-A 3 926 709, the dialkyl carbonate formed during the reaction, together with alkanol and reaction water, is eliminated from the reactor by the reaction gas. EP 460 735 A2 describes a specially dimensioned loop reactor having an external material circulation, which is said not to have the abovementioned disadvantages. However, this reactor easily forms dead zones, especially in the lower bend region, has a high volume, an additional heat exchanger and leakage problems because of the many flange joints. The process described in the two patent applications operates with very high water contents in the reactor, which, according to U. Romano, R. Tesel, M. M. Mauri and P. Rebora (Ind. Eng. Chem. Prod. Res. Dev., (1980), 19, 400), leads to a loss in CO selectivity and increased $CO_2$ production. In EP-A 460 735, for example, in Example 1 a CO selectivity for DMC of only 77% is achieved; the remaining selectivity is apportioned to $CO_2$ formation. In EP-A 460 732, the DMC selectivities achieved with respect to methanol are only 95–97%, as follows from the examples. These disadvantages and the disadvantages already listed for DE-A 3 926 709 mean that this process variant is uneconomic.

A further process problem is separating off the reaction water, for example from methanol and dimethyl carbonate. According to German Offenlegungsschrift 2 450 856, separating off the dimethyl carbonate from the reaction water and methanol using a simple rectification becomes complicated, since various azeotropes are formed between DMC, MeOH and water. The patent application teaches separation by use of an extractive distillation using water as solvent. However, the process is uneconomic, since considerable water quantities are required for the separation (9.5 g of water for 1 g of reaction solution).

SUMMARY OF THE INVENTION

The object was thus to find a process for the preparation of dialkyl carbonates from alkanol, carbon monoxide and oxygen which allows an economic preparation of dialkyl carbonate in particular with high space-time yields and permits a simple continuous separation of the circulated catalyst and the reaction water from the liquid phase.

It has now been found that the reaction can be carried out in a loop reactor having internal material circulation and the catalyst can be separated from the separate reaction solution by simple sedimentation, if the separation is carried out in the temperature range of 20° to 200° C. and at an oxygen partial pressure in the gas phase of at most 5% by volume. It has further been found that, when methanol is the alkanol, the reaction water can be eliminated from the liquid reaction product by simple rectification, the water being produced as bottom product and the azeotrope DMC/methanol and excess methanol being produced as head product.

The present invention therefore relates to a process for the preparation of dialkyl carbonates of the formula

RO—CO—OR            (I)

in which

R represents $C_1-C_{10}$-alkyl, preferably $C_1-C_2$-alkyl, particularly preferably $CH_3$, by reacting the starting alkanol ROH with oxygen and carbon monoxide in the presence of a copper catalyst at elevated temperature and elevated pressure, characterised in that the catalyst in insoluble form is separated off by mechanical separation at 20° to 200° C., preferably at 40° to 150° C., particularly preferably at 40° to 120° C. and at an oxygen partial pressure above the reaction mixture of at most 5% by volume, preferably at most 1% by volume, particularly preferably at most 0.5% by volume and the reaction mixture freed from the catalyst is worked up by rectification.

DETAILED DESCRIPTION OF THE INVENTION

Figure 1:
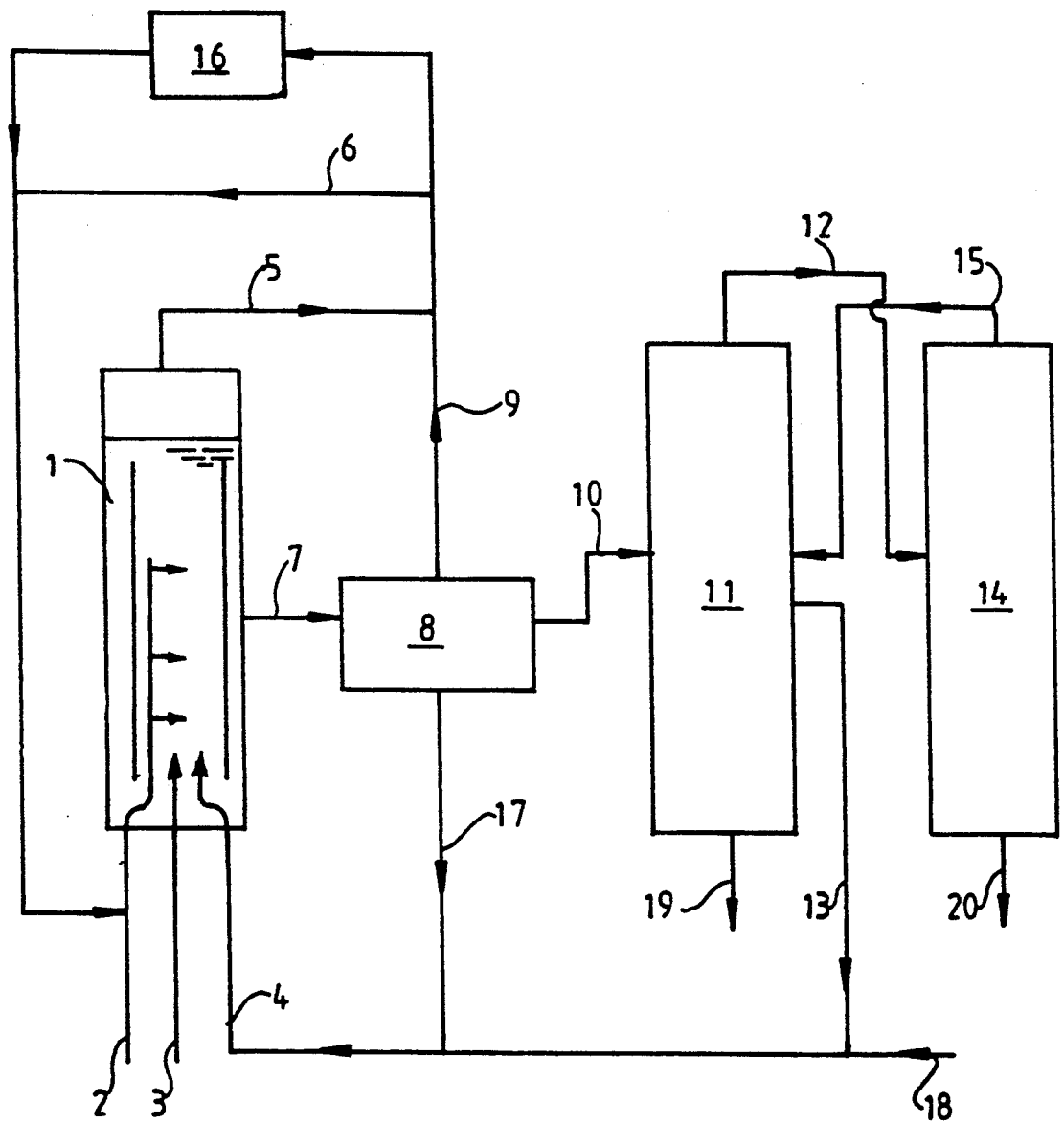

The process according to the invention can be carried out discontinuously or continuously, preferably continuously. The alkanol is reacted in the reactor in the presence of the catalyst with oxygen and carbon monoxide. Inert gas can also be present during this reaction. The inert gas in question can be the constituents of air, apart from $O_2$, and noble gases, additionally $CO_2$ and small quantities of hydrocarbons which can be contained, for example, in a CO from reformers. The dialkyl carbonate formed in the reaction and the reaction water, together with excess alkanol and the catalyst, are withdrawn from the reactor. If the reaction mixture is held at 20° to 200° C. and at an $O_2$ partial pressure above the reaction mixture of at most 5% by volume, an insoluble and quickly sedimenting form of the catalyst is formed The separation of the catalyst from the reaction solution in this insoluble form is carried out by batchwise or continuous sedimentation of the catalyst. Sedimentation in the sense of the invention is taken to mean the separation of the catalyst by the action of the gravitational field of the earth and/or of a centrifugal force field.

Alternatively, the separation of the reaction solution from the sedimented catalyst can, in the discontinuous procedure, also be undertaken in the reactor, for example by decanting or siphoning; the appropriate quantity of alkanol is then resupplied to the catalyst in the reactor and the reaction is carried out again. In this type of procedure, the catalyst remains in the reactor which has the advantage that apparatuses connected downstream do not have to be designed to be corrosion resistant. By connecting two or more discontinuous reactors in parallel, the work-up of the catalyst-free reaction solution is not affected by the discontinuous procedure and can further proceed in the preferred continuous embodiment.

In the preferred continuous embodiment, the catalyst to be recycled, as a suspension, together with fresh and recycled alkanol is supplied to the reactor and at the same time the corresponding quantity of reaction solution and catalyst are withdrawn from the reactor. The reactor used in the preferred embodiment is a loop reactor having internal material circulation, good mixing of the suspension with the gas phase being achieved without stirrer with, at the same time, a low reaction volume.

This type of procedure has the advantage that the reactor can be operated continuously and thus a relatively high space-time yield is possible. Since, as a result of the complete separation of the catalyst, only a few apparatuses are exposed to corrosion, the investment costs are considerably reduced, because of the small number of apparatuses to be made corrosion-resistant, compared with the abovementioned prior art.

The catalyst-free, clear and waterwhite reaction solution thus obtained is freed from the reaction water in a simple rectification, in which, in the case of methanol, for example, the head product obtained is the azeotrope of methanol/DMC and excess methanol and the bottom product obtained is the reaction water; a low-boiling ternary azeotrope of dialkyl carbonate, water and methanol, on the other hand, has not been observed.

In the process according to the invention, the catalysts used are copper compounds based on copper(I) and/or copper(II) salts. These are inorganic or organic Cu salts which can also occur as alkoxy salts with $C_1-C_4$ alkoxy. Since the reaction in question is a redox reaction, both copper ion species are present during the reaction. The copper catalysts used are preferably copper(I) halides, copper(I) acetylacetonate, copper(I) sulphate and/or copper(II) alkoxyhalides, copper(II) alkoxysulphate, copper(II) alkoxyacetylacetonate, particularly preferably copper(I) chloride and/or copper(II) methoxychloride.

The liquid reaction medium is chiefly composed of the $C_1-C_{10}$-alcohol to be reacted, preferably $C_1-C_2$-alkanol and particularly preferably methanol. Generally, the molar ratio, normalised to 1 with respect to alkanol content, of alkanol:dialkyl carbonate:copper (copper from the catalyst suspended and/or dissolved in the reaction mixture) in the reaction mixture at the end of the reaction or on leaving the reactor in continuous operation is 1:(0.005-1):(0.0001-5), advantageously 1:(0.02-0.5):(0.0005-1) and particularly preferably 1:(0.04-0.3):(o.001-0.2).

The reaction of the reaction gases with the alkanol can be conducted at a temperature of 60° to 200° C., preferably 80° to 140° C. and particularly preferably 100° to 130° C.; in this case, normal pressure or elevated pressure can be employed. The reaction is generally carried out at pressures of 1 to 60 bar, preferably 10 to 40 and particularly preferably at 15 to 35 bar. The pressure is expediently produced by compression of the reaction gases.

The gas stream supplied to the reactor can be varied within wide limits, but a total gas stream comprising CO, oxygen and, possibly, an inert gas (such as for example $N_2$, $CO_2$ etc.), based on the copper of the catalyst present in the reaction solution, of 0.2 to 2000 l(S.T.P.)/h per g of Cu and particularly preferably 0.8 to 500 l(S.T.P.)/h per g of Cu is expediently established.

The composition of the reaction gases carbon monoxide and oxygen can be varied within broad concentration ranges, but a $CO:O_2$ molar ratio (normalised to CO) of 1:(0.005-1.0) and preferably 1:(0.01-0.5) is expediently established. The oxygen partial pressure is large enough in these molar ratios to be able to achieve high space-time yields and at the same time is not able to form explosive carbon monoxide/oxygen gas mixtures. The reaction gases are not subject to any particular purity requirements, thus synthesis gas can act as the CO source and air as the $O_2$ carrier, but care must be taken that no catalyst poisons, such as for example sulphur or compounds thereof, are admitted.

The reaction of the catalyst-containing alkanol with the reaction gases under reaction conditions is expediently carried out with as low as possible a concentration of the reaction water unavoidably produced in the reaction mixture, in order to avoid side reactions such as the formation of carbon dioxide and the simultaneous deactivation of the copper catalyst. The reaction water concentration is generally at most 8% by weight, advantageously at most 6% by weight, relative to the liquid phase.

The reaction is conducted up to a desired and adjustable value, relative to the alkanol used, of less than 35% and preferably less than 25% and the reaction solution is separated off from the catalyst in the reactor or, preferably, in a separator.

Separating off the catalyst is expediently carried out in the temperature range of 20° to 200° C., preferably 40° to 150° C. and particularly preferably 40° to 120° C. at a pressure of 0.1 to 60 bar, preferably between 1 and 10 bar and particularly preferably between 1 and 5 bar, the pressure being expediently produced by CO or an inert gas and particularly preferably by the carbon monoxide-containing reactor exhaust gas. The oxygen partial pressure in the gas phase over the reaction mixture here is less than 5% by volume, preferably less than 1% by volume and particularly preferably less than 0.5% by volume. Surprisingly, the catalyst is obtained in a particularly sedimentable form in this method of operating the reactor and/or the separator and, at the same time, a clear, waterwhite and catalyst-free reaction solution is obtained. Neither Cu nor anions of the catalyst can be detected in the separated reaction solution. The remaining catalyst suspension, which is composed of copper(I) chloride and some reaction solution, can be reused without further work-up. This was an unpredictable effect, since according to the prior art, separating off the catalyst from the reaction solution is considered a great problem, and the apparatuses connected downstream therefore must likewise be designed to be corrosion-resistant.

The reaction mixture freed from the catalyst is fractionated by rectification in a manner known in principle.

In an advantageous variant, in the particularly preferred case where R denotes methyl, the catalyst-free reaction solution is freed from the reaction water by simple rectification. This rectification is carried out at 0.1 to 15 bar, preferably 0.8 to 10 bar, particularly preferably at 1 to 5 bar. The column bottom here is heated to 65° to 200° C., preferably 80° to 160° C., particularly preferably 90° to 150° C. Water is obtained as the bottom product here whereas the dimethyl carbonate and excess methanol are obtained as head products. Surprisingly, and in contrast to the relevant literature, none of the azeotropes dimethyl carbonate/methanol/water or dimethyl carbonate/water is obtained, but a separation between dimethyl carbonate and methanol on the one hand and reaction water on the other hand is achieved. Because of the composition of the reaction solution desired according to the invention having excess methanol, in such a distillation, the azeotrope dimethyl carbonate/methanol is first obtained and then further excess methanol is obtained at the head of the column. In a preferred embodiment of this separation by distillation, the azeotrope dimethyl carbonate/methanol is obtained as the head product, the further excess methanol is obtained as a sidestream and the reaction water is obtained as bottom product. The separation of the azeotrope dimethyl carbonate/methanol can then be undertaken in a manner known in principle, for example in a column operated at elevated pressure.

The process according to the invention is described below with reference to FIG. 1 as exemplified by the particularly preferred preparation of dimethyl carbonate:

The reaction of the catalyst-containing reaction mixture of methanol, oxygen and carbon monoxide is carried out in a pressure-resistant and corrosion-resistant reactor (1). Corrosion-resistant reactor materials or cladding materials are, for example, industrial ceramics, enamel, Teflon, tantalum, inconel and other materials known to those skilled in the art. In principle, suitable pressure reactors are also autoclaves having stirrer devices (DE-C 2 743 690, EP 365 083 A1). However, because of the good gas distribution, bubble column reactors and, in particular, loop reactors having internal circulation are also suitable. Because of the slim construction, such loop reactors are especially suitable for medium and high pressures. They are further characterised by the good dispersion of gases and solids and the absence of moving parts (Chem.-Ing.-Tech. 52 (1980), 910/911; Chem.-Ing.-Tech. 62 (1990), 945-947). According to the invention, it is possible to employ both individual reactors and reactor cascades. Carbon monoxide is passed via pipe (2) and oxygen is passed via pipe (3) into the reactor. The apparatuses for dispersing the gases into the suspension present are known and are, for example, jets. It has proved to be advantageous to introduce carbon monoxide and oxygen separately into the reactor. This permits, for example, the metering of the carbon monoxide into the reactor in an advantageous manner simultaneously at different heights (branches of (2)). Methanol, comprising fresh methanol and returned methanol, and the copper-containing catalyst suspended therein are supplied via pipe (4) to the reactor (1). The methanol with the catalyst is preferably also fed to the lower reactor region or between the external and inner tube, as described in FIG. 2. The reactor exhaust gas leaves the reactor (1) via pipe (5) and is fed via the circulation pipe (6) to pipe (2) for repeated exploitation of carbon monoxide and oxygen still present. In case any coformed $CO_2$ is to be eliminated from the circulation gas, a part of this circulation gas can be passed through a $CO_2$ scrubber (16) and then returned. In case carbon monoxide or oxygen is to be diluted with inert gases, an adequate flushing of exhaust gas must obviously be ensured.

Catalyst-containing reaction mixture is withdrawn from the reactor (1) via pipe (7), fed to the separator (8) and expanded. The separator pressure is expediently adjusted by the expanded reaction exhaust gas. The separator exhaust gas is returned via pipe (9) to the circulating gas pipe (6) in compressed form.

Separating off the catalyst can be carried out by sedimentation and/or centrifugation, for example in a hydrocyclone or in hydrocentriclones. Suitable sedimentation vessels are for example single chamber or multiple chamber thickeners (Dorr thickeners), Lamella thickeners, classifiers, conically shaped tanks, tubular sedimentation units and other apparatuses developed therefore (Chem.-Ing.-Tech. 52 (1980), 332: Kirk-Othmer, Encyclopedia of Chemical Technology, Vol. 20, Third Edition, John Wiley & Sons, New York 1982). Suitable centrifuges are: decanters, disk centrifuges, overflow and scraper type centrifuge and others. The thickened catalyst suspension is returned via pipe (17) together with fresh methanol (18) and returned methanol (13) via pipe (4) to the reactor (1).

A clear, catalyst-free reaction solution, comprising dimethyl carbonate, excess methanol and reaction water, flows via pipe (10) out of the separator (8) into the distillation column (11). Separation is carried out in (11) into the reaction water as bottom product (19), into methanol, which is withdrawn in a sidestream (13) and returned to the reaction, and into dimethyl carbonate/methanol azeotrope as head product. Suitable columns are, for example, packed columns, bubble cap columns and others. The dimethyl carbonate/methanol azeotrope departing as head product is passed via pipe (12) to the dimethyl carbonate column (14). A fractionation known per se of the dimethyl carbonate/methanol azeotrope is carried out in (14), for example by distillation at elevated pressure. Dimethyl carbonate is withdrawn as the bottom product (20) from (14). The head product (15) produced from (14) is a dimethyl carbonate-depleted methanol, which is returned via pipe (15) to the distillation column (11). The dimethyl carbonate (20) obtained in this manner is of high purity and can be supplied to many intended applications without further purification.

Figure 2:
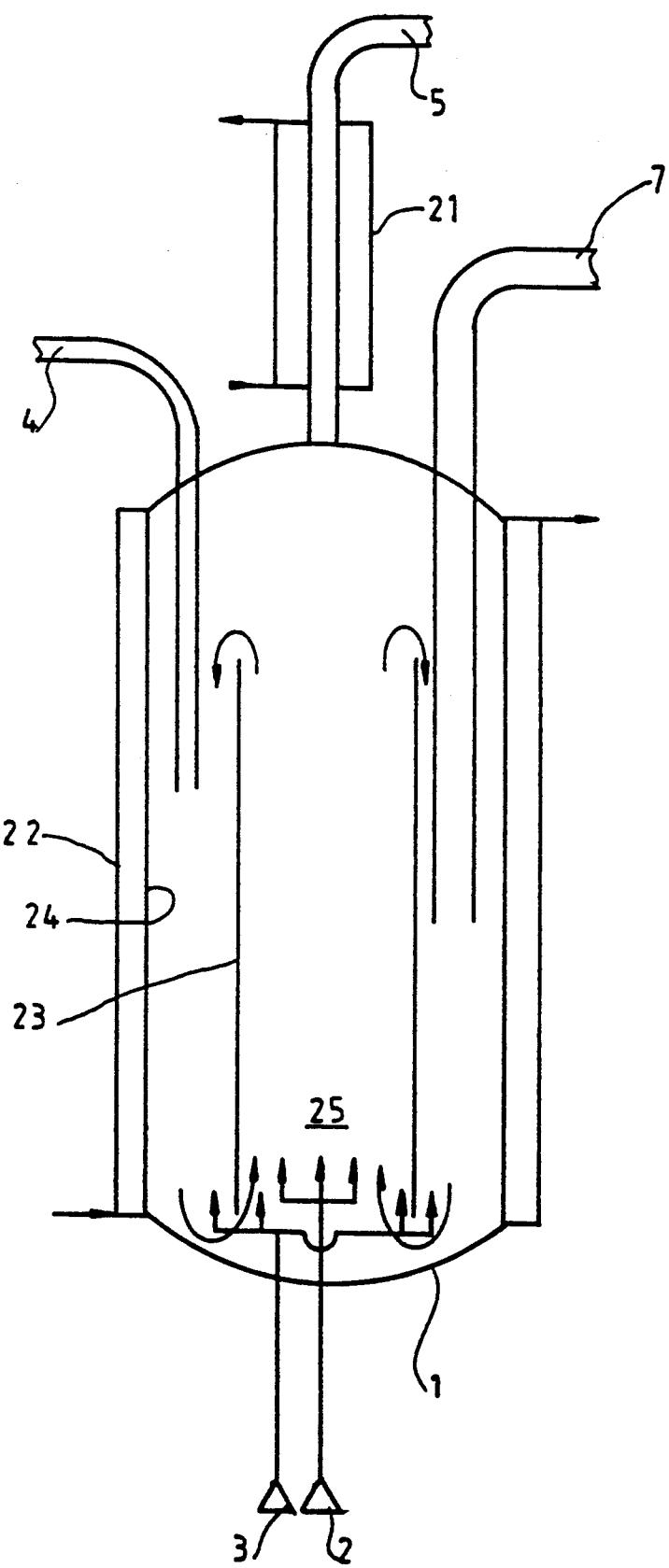

In FIG. 2, the reactor preferably used according to the invention is represented diagrammatically.

The reactor (1), comprising an inner tube (central tube (23) or a plurality of inner tubes and an outer tube (24) having a heat exchange surface (22) is supplied via pipe (2) with carbon monoxide in the inner tube(s). The oxygen metering is carried out separately via pipe (3) in an annular manner into the inner and/or outer tube. The gas distribution (25) is carried out according to the prior art, for example, by jets, slits, frits, sieves etc. As a result of the gas quantity metered into the inner tube of 500–30,000 l(S.T.P.)/l of liquid volume, preferably 800–20,000 l(S.T.P.)/l of liquid volume and particularly preferably 1000–15,000 l-(S.T.P.)/l of liquid volume, the suspension is conveyed according to the principle of the airlift pump. Fresh methanol, returned methanol and recycled and, possibly, fresh catalyst is fed via pipe (4). At the same time, a corresponding amount of reaction solution and catalyst is withdrawn via pipe 7, which has a comparatively large cross-sectional area. As a result of the dimensioning and the withdrawal against gravity, a large part of the catalyst is already separated from the reaction solution. The remaining catalyst is separated off as described by sedimentation.

Unreacted reaction gas leaves the reactor via pipe (5), entrained liquid and vapour being condensed at the condenser (21). Heating the reactor is carried out via the heat exchange surface (22).

The loop reactor preferably to be used according to the invention and having internal material circulation (internal loop) is, in the preferred embodiment, a slim reactor having a height of 0.1 to 40 m, preferably 0.5–30 m and particularly preferably 1 to 20 m, with a diameter of the outer tube of 0.1–5 m, preferably 0.3–4 m and particularly preferably 0.5–2 m. The ratio of the volumes of the inner tube, or tubes to the outer tube circulation volume is 0.1–5, preferably 0.2 to 3 and particularly preferably 0.5 to 2.

EXAMPLE 1

1000 ml of methanol were reacted with oxygen and carbon monoxide at 30 bar and 120° C. in a 2 l tantalum autoclave equipped with stirrer. The catalyst used was $Cu_2Cl_2$ at a rate of 1.62 mol/liter of methanol The flow rates of carbon monoxide and oxygen were 120 and 6.3 l(S.T.P.)/h, respectively. The reaction mixture was agitated by the stirrer and the flow of the reaction gases. After a reaction time of 4 h, the autoclave was emptied under protective gas.

The catalyst was separated off from the clear and water-white reaction solution under CO gas (1 bar) by sedimentation and decanting at 40° C. The analysis of the reaction solution gave the following composition (in % by weight): 75% MeOH, 20.6% DMC and 4.4% $H_2O$. Copper ions and chloride ions could not be detected. The exhaust gas of the autoclave consisted solely of CO (95–99%), $CO_2$ (0.04–1%) and $O_2$ (0–0.8%). Methyl chloride and dimethyl ether could only be detected in very low amounts (0.006–0.03% by volume in a plurality of repeat experiments). The analysis of the white catalyst gave the composition as $Cu_2Cl_2$ with some water.

EXAMPLE 2

The reaction was carried out analogously to Example 1, but with the difference that instead of the copper(I) chloride, copper methoxychloride was used as catalyst, which had been prepared in the autoclave by preoxidation of the CuCl used (1.62 mol/l of MeOH) with oxygen (1.1 mol) at 120° C. and 20 bar of nitrogen admission pressure.

The work-up was then carried out analogously to Example 1.

The analysis of the clear, waterwhite and catalyst-free reaction solution gave the following composition: 68% MeOH, 26% DMC and 6.0% water. The selectivity, relative to CO, was 93.1% for DMC and 6.9% for $CO_2$.

Analysis of the white catalyst gave: 63.0% Cu, 33.7% Cl, <0.1% C, 0.3% H and 2.9% $O_2$.

A suspension sample (23 g) withdrawn from the reactor during the reaction sedimented, with exclusion of air (flushing with CO), immediately at 40° C. Another suspension sample (39 g) withdrawn, which under conventional conditions (no CO flushing) should sediment with air contact, could neither be sedimented nor filtered. A separation of the catalyst could only be achieved by distilling off the reaction solution.

EXAMPLE 3

Methanol was reacted with oxygen and carbon monoxide analogously to Example 2 at 30 bar and 120° C. in the autoclave described in Example 1. In contrast to Example 2, the autoclave was not opened at the end of reaction, but, following cooling and sedimentation of the catalyst (T=50° C.), the reaction solution was eliminated from the autoclave via a rising pipe.

After addition of fresh methanol, the reaction was carried out analogously to Example 1.

This procedure was carried out a total of four times and on the 5th cycle, the autoclave was emptied analogously to Example 1.

The results of the experiment are compiled in Table 1. In all cases, clear and waterwhite reaction solutions were obtained. In this case, the Cu and Cl contents in the reaction solutions were also under the detection limit.

The exhaust gas compositions corresponded to those of Example 2.

TABLE 1

| No. | Individual running time h | DMC content of the reaction solution % by wt. | Selectivities relative to MeOH for DMC | relative to CO for DMC | relative to CO for $CO_2$ |
|---|---|---|---|---|---|
| 1 | 2 | 18.3 | >99 | 90.8 | 9.2 |
| 2 | 4 | 22.2 | >99 | 92.4 | 7.6 |
| 3 | 4 | 27.7 | >99 | 93.4 | 6.6 |
| 4 | 5 | 28.5 | >99 | 92.6 | 7.4 |
| 5 | 5 | 28.9 | >99 | 90.9 | 9.1 |

DMC = dimethyl carbonate; MeOH = methanol

EXAMPLE 4

125 g of catalyst-free reaction solution from Example 4 were distilled in a distillation apparatus comprising a two-necked flask, 15 cm packed column having 8 cm packing height (4 mm Berl saddles), Claisen stillhead and fraction collector. The reaction solution had the following composition: 70.9% of MeOH, 23.8% DMC, 5.3% $H_2O$. Even using this simple arrangement, the following separation result was achieved (Table 2):

TABLE 2

| Fraction | Temperature Bottom | Temperature Head | Amount g | Composition in % by wt. MeOH | Composition in % by wt. DMC | Composition in % by wt. $H_2O$ |
|---|---|---|---|---|---|---|
| 1 | 100 | 64 | 105.33 | 71.1 | 28.6 | 0.3 |
| 2 | 100 | 64 | 8.79 | 98.2 | 0.7 | 1.0 |
| Remainder | — | — | 10.70 | 42.4 | 0.0 | 57.6 |

EXAMPLE 5

A catalyst-free solution of the following composition: 71.4% MeOH, 23.8% DMC and 4.8% water was distilled in a distillation apparatus comprising a three-necked flask, a 100 cm-long column packed with 4×4 mm V2A wire mesh rolls and fraction collector.

64.6 g of solution were withdrawn for analysis from the bottom during the experiment. The following result was achieved in the distillation:

TABLE 3

| Fraction | Temperature Bottom | Temperature Head | Amount g | Composition in % by wt. MeOH | Composition in % by wt. DMC | Composition in % by wt. $H_2O$ |
|---|---|---|---|---|---|---|
| 1 | 107 | 64.1 | 382.7 | 70.7 | 29.3 | <0.1 |
| 2 | 107 | 64.7 | 69.6 | 92.0 | 8.0 | <0.1 |
| Remainder | — | — | 27.9 | 45.7 | 0.0 | 54.3 |

What is claimed is:

1. A process for the preparation of a dialkyl carbonate of the formula

RO—CO—OR in which represents $C_1$-$C_{10}$-alkyl, by reacting the starting alkanol ROH with oxygen and carbon monoxide in the molar ratio of $CO:O_2$1:0.005-1 in the presence of a copper catalyst at a temperature of 60°-200° C. and a pressure of 1-60 bar, wherein the reaction mixture withdrawn from the reactor has the molar composition alkanol:dialkyl carbonate:Cu=1:0.005-1:0.0001-5, the catalyst in insoluble form is separated off by mechanical separation at 20° C. to 200° C., at a pressure of 0.1-60 bar and at an oxygen partial pressure above the reaction mixture of at most 5% by volume and the reaction mixture freed from the catalyst is worked up by rectification.

2. The process of claim 1, wherein the dialkyl carbonate to be prepared is of the formula

RO—CO—OR, in which

R represents $C_1$-$C_2$-alkyl.

3. The process of claim 2, wherein the dialkyl carbonate to be prepared is of the formula

RO—CO—OR in which

R represents $CH_3$.

4. The process of claim 1, wherein the catalyst is separated off at 40°-150° C.

5. The process of claim 1, wherein the catalyst is separated off at a pressure of 1-10 bar.

6. The process of claim 1, wherein the oxygen partial pressure above the reaction mixture is at most 1% by volume.

7. The process of claim 6, wherein the oxygen partial pressure above the reaction mixture is at most 0.5% by volume.

8. The process of claim 1, wherein Cu(I) compounds and/or Cu(II) compounds selected from the group comprising the inorganic and organic Cu salts and alkoxy salts of Cu are fed in as catalyst.

9. The process of claim 1, wherein the mechanical separation carried out is decanting or siphoning after sedimentation filtration or centrifuging.

10. The process of claim 1, wherein the reaction is carried out at 80° to 140° C.

11. The process of claim 1, wherein the reaction is carried out at 10–40 bar.

12. The process of claim 1, wherein the reaction mixture withdrawn from the reactor has the molar composition alkanol:dialkyl carbonate: Cu=1:0.02-5:0.005-1.

13. The process of claim 12, wherein the reaction mixture withdrawn from the reactor has the molar composition alkanol:dialkyl carbonate: Cu=1:0.04-0.3:0.001-0.2.

14. The process of claim 1, wherein carbon monoxide and oxygen are used in the molar ratio $CO:O_2$=1:0.01-0.5.

15. The process of claim 1, wherein a concentration of the reaction water in the reaction mixture is established of at most 8% by weight, relative to the weight of the liquid reaction mixture.

16. The process of claim 15, wherein the concentration of the reaction water is at most 6% by weight, relative to the weight of the liquid reaction mixture.

17. The process of claim 1, wherein in the case of R=$CH_3$, the reaction water is discharged as bottom product in the rectification at 0.1-15 bar and a bottom temperature of 65°-200° C.

18. The process of claim 1, wherein the reaction proceeds to a value of less than 33% of the alkanol used.

19. The process of claim 18, wherein the reaction proceeds to a value of less than 25% of the alkanol used.

20. The process of claim 1, wherein a loop reactor having internal material circulation is used of height 0.1-40 m, at a diameter of the outer tube of 0.1-5 m and a ratio of the volume of the inner tube or tubes to the outer material circulation volume of 0.1-5.

* * * * *

UNITED STATES PATENT AND TRADEMARK OFFICE
CERTIFICATE OF CORRECTION

PATENT NO. : 5,274,163
DATED : December 28, 1993
INVENTOR(S) : Johann Rechner et al It is certified that error appears in the above-indentified patent and that said Letters Patent is hereby corrected as shown below:

| | |
|---|---|
| Title Page Foreign Pat. Doc.s | Delete "02176541" and substitute -- 0217651 -- |
| Col. 9, line 58 | Before "represents" insert -- R -- |
| Col. 9, line 60 | After "CO:$O_2$" insert -- = -- |
| Col. 10, line 33 | After "sedimentation" insert -- , -- |
| Col. 10, line 40 | Delete "Cu=1:0.02-5:0.005-1" and substitute -- Cu=1:0.02-5:0.0005-1 -- |

Signed and Sealed this

Thirteenth Day of June, 1995

Attest:

BRUCE LEHMAN

Attesting Officer     Commissioner of Patents and Trademarks